United States Patent [19]

Umminger et al.

[11] Patent Number: 4,621,098

[45] Date of Patent: Nov. 4, 1986

[54] THIOETHERS AND PHARMACEUTICAL COMPOSITIONS CONTAINING THEM

[75] Inventors: Robert Umminger, Mannheim; Walter-Gunar Friebe, Darmstadt; Wolfgang Kampe, Heddesheim; Androniki Roesch, Mannheim; Otto-Henning Wilhelms, Weinheim-Rittenweier, all of Fed. Rep. of Germany

[73] Assignee: Boehringer Mannheim GmbH, Mannheim, Fed. Rep. of Germany

[21] Appl. No.: 626,690

[22] Filed: Jul. 2, 1984

[30] Foreign Application Priority Data

Jul. 9, 1983 [DE] Fed. Rep. of Germany ....... 3324916

[51] Int. Cl.$^4$ ................ C07C 147/107; A61K 31/195
[52] U.S. Cl. .................... 514/562; 568/30; 514/232; 568/31; 514/532; 568/32; 568/33; 514/534; 568/36; 568/37; 514/538; 568/38; 514/541; 514/543; 568/42; 514/568; 568/43; 514/571; 568/44; 514/618; 568/46; 568/51; 514/676; 568/55; 514/678; 568/57; 568/62; 514/545; 568/63; 568/64; 514/685; 568/67; 514/688; 514/689; 514/706; 514/712; 514/713; 544/158; 560/11; 560/12; 560/13; 560/15; 560/16; 560/18; 562/426; 562/428; 562/429; 562/431; 562/432; 568/27; 568/29
[58] Field of Search ...................... 560/12, 13, 15, 16; 562/426, 430, 431, 432, 429; 424/308, 309, 317, 319, 337; 514/562, 570, 709, 712, 571, 685; 568/31

[56] References Cited

U.S. PATENT DOCUMENTS 2,801,972 8/1957 Bartlett ............................... 562/426
3,793,365 2/1974 Winter .................................. 562/426
3,983,171 9/1976 Vanlerberghe ..................... 562/426

OTHER PUBLICATIONS

Soper, J. Am. Chem. Soc., 70, pp. 2849-2855 (1948).

Primary Examiner—Michael L. Shippen
Attorney, Agent, or Firm—Felfe & Lynch

[57] ABSTRACT

The present invention provides thioethers of the general formula:

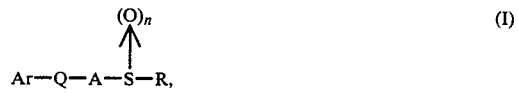

wherein Ar is a phenyl radical which is optionally substituted one, two or three times by alkyl, alkenyl, alkoxy, alkylthio, alkanoyl, hydroxyl, hydroxyalkyl, carboxyl, alkoxycarbonyl, carbamoyl, nitro, amino or halogen, Q is an oxygen or sulphur atom or an NH group, A is a straight-chained or branched $C_2$-$C_8$ alkylene radical which is optionally substituted by a hydroxyl group or can be interrupted by an ethenylene or ethynylene group, n is 0, 1 or 2, and R is a hydrogen atom or a straight-chained or branched alkyl radical which is optionally substituted one or more times by the same or different radicals selected from alkoxycarbonyl, alkoxy, hydroxyl, carboxyl or optionally substituted carbamoyl or amino; as well as the pharmacologically acceptable salts thereof, with the proviso that A cannot be ethylene when Ar is a phenyl radical, Q is an oxygen atom and R is the group —$CH_2COOH$.

The present invention also provides processes for the preparation of these compounds and pharmaceutical compositions containing them.

15 Claims, No Drawings

THIOETHERS AND PHARMACEUTICAL COMPOSITIONS CONTAINING THEM

The present invention is concerned with new thioethers, processes for the preparation thereof and pharmaceutical compositions containing them.

The compounds according to the present invention can, in the case of oral and parenteral administration, inhibit anaphylactic and anaphylactoid reactions, such as can be initiated, for example, in sensitised guinea pigs by allergen provocation. Furthermore, they inhibit inflammation. Therefore, they are useful for combating allergic diseases, for example allergic asthma.

2-Phenyloxyethylmercaptoacetic acid is known from J.A.C.S., 70, 2849/1948, as an intermediate for the preparation of penicillins.

According to the present invention, there are provided thioethers of the general formula:

$$Ar-Q-A-\overset{(O)_n}{\underset{|}{S}}-R,$$  (I)

wherein Ar is a phenyl radical which is optionally substituted one, two or three times by alkyl, alkenyl, alkoxy, alkylthio, alkanoyl, hydroxyl, hydroxyalkyl, carboxyl, alkoxycarbonyl, carbamoyl, nitro, amino or halogen, Q is an oxygen or sulphur atom or an NH group, A is a straight or branched chain $C_2$-$C_8$ alkylene radical which is optionally substituted by a hydroxyl group or can be interrupted by an ethenylene or ethynylene group, n is 0, 1 or 2 and R is a hydrogen atom or a straight or branched chain alkyl radical which can be substituted by one or more identical or different radicals selected from alkoxycarbonyl, alkoxy, hydroxyl, carboxyl and optionally substituted carbamoyl or amino; as well as the pharmacologically acceptable salts thereof, with the proviso that A cannot be ethylene when Ar is a phenyl radical, Q an oxygen atom and R the group —CH$_2$COOH.

The present invention also provides pharmaceutical compositions containing at least one compound of general formula (I), in admixture with a solid or liquid pharmaceutical diluent or carrier. The present invention is also concerned with the use of compounds of general formula (I) for the production of such compositions.

The alkyl radicals in all of the above-mentioned groups of Ar and R, whether alone or as a component of alkoxy, alkylthio, alkanoyl, alkoxycarbonyl or hydroxyalkyl radicals, contain up to 12 and preferably up to 4 carbon atoms and can be straight or branched chained. Preferred radicals include methyl, ethyl, propyl and pentyl; methoxy and ethoxy; methylthio; acetyl and propionyl; carbomethoxy and carboethoxy; and hydroxymethyl and hydroxyethyl. The alkylene radical contains 2 to 6 carbon atoms and is preferably an allyl radical.

The halogen atom is a fluorine, chlorine or bromine atom.

A substituted carbamoyl group of the substituent R preferably means a 2-(4-morpholino)-ethyl or 2-(dimethylamino)-ethyl radical. A substituted amino group of the substituent R is preferably a trifluoroacetylamino or dimethylamino radical.

In particular, the substituent R has one of the following meanings: —CH$_2$COOH, —CH$_2$—CH$_2$—COOH, —CH$_2$—CH(CH$_3$)—COOH, —(CH$_2$)$_5$—COOH, —(CH$_2$)$_{12}$—COOH, —CH$_2$—CH(NH$_2$)—COOH, —CH(COOH)—CH$_2$—COOH, —CH$_2$—CH$_2$OH, —CH$_2$—CH(OH)—CH$_2$OH, —CH(CH$_3$)—CH$_2$—CH$_3$,

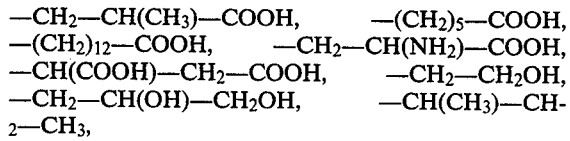

—CH$_2$CH$_2$—CO—NH—CH$_2$CH$_2$—N(CH$_3$)$_2$ or —CH$_2$CH$_2$—N(CH$_3$)$_2$.

The group A preferably has one of the following meanings: —CH$_2$CH$_2$—, —CH$_2$CH$_2$CH$_2$—, —CH$_2$—CH(OH)—CH$_2$— —CH$_2$CH$_2$CH$_2$CH$_2$—, —CH$_2$—CH=CH—CH$_2$— or —CH$_2$—C≡C—CH$_2$—.

Especially preferred are compounds with the above-given meanings of Ar, A and R in which Q is an oxygen atom and n is 0. Apart from the compounds mentioned in the following Examples, the present invention also includes, in particular, all compounds which have every possible combination of the substituents mentioned in the Examples.

The present invention also provides a process for the preparation of the compounds of general formula (I), wherein (a) a compound of the general formula:

Ar—Q—H    (II), in which Ar and Q have the same meanings as above, is reacted with a compound of the general formula:

X—A—Y    (III), in which A has the same meaning as above and X and Y are reactive residues and, when A stands for the radical —CH$_2$CH(OH)CH$_2$—, X—A—Y can also be

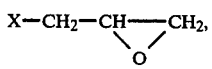

and with a compound of the general formula:

R—S—H    (IV), in which R has the same meaning as above; or (b) a compound of the general formula:

Ar—Q—A—SH    (V), in which Ar, Q and A have the same meanings as above, is reacted with a compound of the general formula:

R—X    (VI), in which R and X have the same meanings as above, whereafter, if desired, the sulphur is oxidised or the substituent R is converted, for example when R is substituted by alkoxycarbonyl is optionally saponified to carboxyl, when R contains a protected amino function the protective group is optionally split off and when R is alkoxy-substituted, it is optionally converted into a hydroxyl group; and the reaction product obtained is, if desired, converted into a pharmacologically acceptable salt.

The reactive residues X and Y in the compounds of general formula (III) can be, for example, chlorine, bromine, mesyloxy or tosyloxy.

The processes according to the present invention are carried out, for example, by first reacting a compound of general formula (II) with a compound of general formula (III) and the reaction product obtained is isolated. This intermediate is then reacted with a compound of general formula (IV). The reaction preferably takes place in a neutral or basic medium, for example in a lower alcohol, such as methanol, with or without the addition of triethylamine, or in a lower alcohol, such as ethanol, in the presence of an alkali metal alcoholate.

According to another variant, a compound of general formula (IV) is first alkylated with a compound of general formula (III) and the intermediate obtained is subsequently reacted with a compound of general formula (II).

According to another process, a compound of the general formula (V), which can be obtained by reacting a compound of general formula (II) with a compound of general formula (III) and subsequently converting the remaining group X or Y into an —SH group, is reacted with a compound of general formula (VI). The reaction is preferably carried out in a neutral or basic medium, for example in a lower alcohol, such as methanol, with or without the addition of triethylamine, or in a lower alcohol, such as ethanol, in the presence of an alkali metal alcoholate.

A subsequent conversion of compounds of general formula (I) can, for example, take place according to known methods, by oxidising a sulphide to the corresponding sulphoxide or sulphone.

A further possibility of subsequently converting compounds of general formula (I) consists in that one or more substituents of the group R in compounds of general formula (I) are converted by esterification, saponification, reduction, alkylation, acylation, hydrogenolysis, oxidation, amidation or elimination into one or more other substituents of the radical R.

The starting materials of general formulae (II), (III), (IV) and (VI) are either known from the literature or can be prepared analogously to processes known from the literature.

As pharmacologically-acceptable salts, there are especially preferred the alkali metal, alkaline earth metal and ammonium salts, as well as possibly salts with non-toxic inorganic and organic acids, for example, hydrochloric acid, sulphuric acid, phosphoric acid, hydrobromic acid, acetic acid, lactic acid, citric acid, malic acid, benzoic acid, salicylic acid, malonic acid, maleic acid, succinic acid or diaminocaproic acid.

The salts are obtained in the usual manner, for example by neutralisation of compounds of general formula (I) with the appropriate acids or bases.

For the preparation of pharmaceutical compositions, the compounds of general formula (I) are mixed in known manner with appropriate pharmaceutical carrier substances, aroma, flavouring and colouring materials and shaped, for example, into tablets or dragees or, with the addition of appropriate adjuvants, are suspended or dissolved in water or in an oil, such as olive oil.

The compounds of general formula (I) can be administered orally or parenterally in liquid or solid form. As injection medium, it is preferred to use water which contains the stabilising agents, solubilising agents and/or buffers usual in the case of injection solutions. Such additives include, for example, tartrate and borate buffers, ethanol, dimethyl sulphoxide, complex formers (such as ethylenediaminetetraacetic acid), high molecular weight polymers (such as liquid polyethylene oxide) for viscosity regulation and polyethylene derivatives of sorbitol anhydrides.

Solid carrier materials include, for example, starch, lactose, mannitol, methyl cellulose, talc, highly dispersed silicic acid and high molecular weight polymers (such as polyethylene glycols).

Compositions suitable for oral administration can, if desired, contain flavouring and sweetening agents. For external administration, the compounds of general formula (I) according to the present invention can also be used in the form of powders and salves. For this purpose, they are mixed, for example, with powdery, physiologically compatible dilution agents or with conventional salve bases.

The dosage administered depends upon the age, state of health and weight of the recipient, the extent of the disease, the nature of possibly simultaneously carried out further treatments, the frequency of the treatment and the nature of the desired action. Usually, the daily dosage of the active compound is 0.1 to 50 mg./kg. of body weight. Normally, 0.5 to 40 and preferably 1.0 to 20 mg./kg./day in one or more administrations per day are effective for obtaining the desired results.

The compounds can be used as such or they can be converted to salts with pharmacologically acceptable acids. They can be administered to patients orally, as pills, tablets, capsules, powders and the like. The preferred form of oral administration is a tablet containing 10 to 300 mg of active compound, which is the range of typical daily dosages. The preferred content or dosage is 30 to 100 mg.

The compounds can also be administered parenterally. Injection solutions (normally aqueous) containing the active compound in an amount of 0.05 to 50 mg/ml of injection solution are administered.

EXPERIMENTAL PROCEDURE

The superior activity of the novel compounds is shown by comparing the inhibition of antigen induced bronchospasms in passively sensitized guinea pigs. Specifically, tests were run as follows:

PREPARATION OF ANTISERUM

The antigen is twice recrystallized egg albumin. Equal volumes of saline solution of antigen (5 mg/ml) and Freund's complete adjuvant were emulsified and 0.15 ml injected into each hind foot of adult male guinea pigs (Davies and Johnson: *Int. Arch. Allergy*, 41, 648–654, 1971).

The animals were bled and the pooled serum stored at −20° C.

PASSIVE SENSITIZATION

Injections of 0.5 ml antiserum of 1:50 dilution were given i.v. 24–48 hrs. before challenge.

Guinea pigs were anaesthetized with pentobarbitone sodium (40 mg/kg i.p.). Cannulae were tied into the trachea and the jugular vein and the lung inflated with a pump at a rate of 72 strokes/min. and a constant stroke volume of 6–8 ml.

Bronchospasm, provoked by injecting ovalbumim i.v. was measured as described by Konzett Rössler (Versuchsanordnung zu Untersuchungen an der Bronchialmuskulat Naunyn-Schmiedebergs Arch. exp. Path. Pharmak. 195, 71–74, 1940), and modified by Collier and James (Collier, H. O. J., J. A. Holgate, M. Schachter: The Bronchoconstrictor Action of Bradykinin in the Guinea-Pig, *Brit. J. Pharmacol.*, 15, 290, 1960).

Drugs were applied p.o. 75 minutes before antigen. For calculation the following formula was used:

$$\% \text{ Bronchospasm } \frac{b-a}{m-a} \times 100$$

b=Bronchospasm after antigen injection, measured in mm from tracing m=Maximum height of tracing in mm with arm of the trachea-cannula clamped a=pre-injection height of the tracing in mm Percent (%) inhibition of bronchospasm was calculated by comparing control groups with drug pretreated groups 3 minutes after antigen application.

| Example | Dose (mg/kg) | Inhibition of BrSp (%) |
|---|---|---|
| 2i | 3.0 | 63 |
| 9 | 3.0 | 43 |
| 6e | 3.0 | 53 |
| 17 | 3.0 | 56 |
| 2r | 3.0 | 52 |
| 4i | 3.0 | 54 |
| *Tiaramide | 100.0 | 0 |
|  | 200.0 | 17 |

Inhibition of antigen induced bronchospasm (BrSp) in passively sensitized guinea pig

*4-[(5-chloro-2-oxo-3(2H)—benzothiazolyl)acetyl]-1-piperazineethanol (U.S. Pat. No. 3 661 921)

Preparation of the compounds is exemplified in the following:

EXAMPLE 1

S-[4-(4-Acetyl-3-hydroxy-2-propylphenoxy)-butyl]-3-mercaptopropionic acid

A miture of 5.5 g. (17 mmol) 4-(4-acetyl-3-hydroxy-2-propylphenoxy)-n-butyl bromide, 1.9 g. (18 mmol) 3-mercaptopropionic acid, 7.25 g. (70 mmol) triethylamine and 25 ml. methanol is heated under reflux for 4 hours. After cooling, the reaction mixture is mixed with water, acidified and extracted with dichloromethane. The organic phase is washed neutral, dried and evaporated. The residue is taken up with dichloromethane and chromatographed on silica gel (elution agent: dichloromethane/methanol 98:2 v/v). After trituration with diethyl ether, there are obtained 2.8 g. (46% of theory) S-[4-(4-acetyl-3-hydroxy-2-propylphenoxy)-butyl]-3-mercaptopropionic acid; m.p. 75°–77° C.

EXAMPLE 2

The following compounds are obtained in a manner analogous to that described in Example 1:

| | designation | Yield % | m.p. °C. (solvent) |
|---|---|---|---|
| a | S—[3-(3-chlorophenoxy)-propyl]-3-mercapto-propionic acid from 3-(3-chlorophenoxy)-propyl bromide and 3-mercapto-propionic acid | 69 | 40–42 (dichloromethane) |
| b | S—[3-(3-nitrophenoxy)-propyl]-3-mercapto-propionic acid from 3-(3-nitrophenoxy)-propyl bromide and 3-mercapto-propionic acid | 44 | 58–61 (diethyl ether) |
| c | S—[3-(2-pentylphenoxy)-propyl]-3-mercapto-propionic acid from 3-(2-pentylphenoxy)-propyl bromide and 3-mercapto-propionic acid | 31 | 35–37 (dichloromethane) |
| d | S—[3-(4-acetyl-3-hydroxy-phenoxy)-propyl]-2-mercapto-ethanol from 3-(4-acetyl-3-hydroxyphenoxy)-propyl bromide and 2-mercapto-ethanol | 82 | 50–52 (diethyl ether) |
| e | S—[3-(4-acetyl-3-hydroxy-phenoxy)-propyl]-3-mercapto-propionic acid from 3-(4-acetyl-3-hydroxyphenoxy)-propyl bromide and 3-mercaptopropionic acid | 58 | 116–119 amorphous (diethyl ether) |
| f | S—[3-(4-acetyl-2-allyl-3-hydroxyphenoxy)-propyl]-2-mercaptoethanol from 3-(4-acetyl-2-allyl-3-hydroxy-phenoxy)-propyl bromide and 2-mercaptoethanol | 51 | 61–63 (methanol) |
| g | S—[3-(4-acetyl-2-allyl-3-hydroxyphenoxy)-propyl]-2-hydroxy-3-mercaptopropanol from 3-(4-acetyl-2-allyl-3-hydroxyphenoxy)-propyl bromide and 2-hydroxy-3-mercaptopropanol | 84 | 58–60 (diethyl ether) |
| h | S—[3-(4-acetyl-3-hydroxy-2-propylphenoxy)-propyl]-3-mercaptopropionic acid from 3-(4-acetyl-3-hydroxy-2-propylphenoxy)-propyl bromide and 3-mercapto-propionic acid | 75 | 90–93 (diethyl ether) |
| i | S—[3-(4-acetyl-2-allyl-3-hydroxyphenoxy)-propyl]-3-mercaptopropionic acid from 3-(4-acetyl-2-allyl-3-hydroxyphenoxy)-propyl bromide and 3-mercaptopropionic acid | 53 | 96–99 (methanol) |
| j | S—[3-(4-acetyl-3-hydroxy-2-propylphenoxy)-propyl]-DL-mercaptosuccinic acid from 3-(4-acetyl-3-hydroxy-2-propylphenoxy)-propyl bromide and DL-mercaptosuccinic acid | 47 | 126–128 (methanol/water) |
| k | S—[4-(4-acetyl-3-hydroxy-2-propylphenoxy)-n-butyl]-2-mercaptoethanol from 4-(4-acetyl-3-hydroxy-2-propylphenoxy)-n-butyl bromide and 2-mercaptoethanol | 64 | oil |
| l | S—[3-(4-methylmercapto-phenoxy)-propyl]-3-mercapto-propionic acid from 3-(4-methylmercaptophenoxy)-propyl bromide and 3-mercaptopropionic acid | 29 | 62–64 (diethyl ether) |
| m | S—[3-(2-(2-hydroxyethyl)-phenoxy)-propyl]-3-mercapto-propionic acid from 3-[2-(2-hydroxyethyl)-phenoxy]-propyl bromide and 3-mercaptopropionic acid | 34 | 86–88 (diethyl ether/ligroin) |
| n | S—[3-(2-carboxyphenoxy)-propyl]-3-mercaptopropionic acid from 3-(2-carboxyphenoxy)-propyl bromide and 3-mercaptopropionic acid | 77 | 83–85 (diethyl ether) |

-continued

| | designation | Yield % | m.p. °C. (solvent) |
|---|---|---|---|
| o | S—[3-(2-ethoxycarbonyl-phenoxy)-propyl]-3-mercapto-propionic acid from 3-(2-ethoxycarbonylphenoxy) propyl bromide and 3-mercaptopropionic acid | 51 | 46–49 (diethyl ether/ ligroin) |
| p | S—[3-(2-carbamoylphenoxy)-propyl]-3-mercapto-propionic acid from 3-(2-carbamoyl-phenoxy)-propyl bromide and 3-mercaptopropionic acid | 57 | 114–116 (ethyl acetate) |
| q | S—[3-(3-pentylphenoxy)-propyl]-3-mercaptopropionic acid from 3-(3-pentyl-phenoxy)-propyl bromide and 3-mercaptopropionic acid | 38 | Na salt 176–181 amorphous |
| r | 2-{3-[S—(2-butyl)-mercapto]-propoxy}-benzoic acid from 2-(3-bromopropoxy)-benzoic acid and 2-butylmercaptan | 52 | Na salt 271 (decomp.) amorphous |
| s | S—[3-(4-acetyl-3-hydroxy-2-propylphenoxy)-propyl]-3-mercapto-2-methylpropionic acid from 3-(4-acetyl-3-hydroxy-2-propylphenoxy)-propyl bromide and 3-mercapto-2-methylpropionic acid | 41 | 90–93 (decomp.) Na salt amorphous |

EXAMPLE 3

S-[3-(3-methoxyphenoxy)-propyl]-3-mercaptopropionic acid 2.65 g. (25 mmol) 3-mercaptopropionic acid are added at ambient temperature to a solution of 1.15 g (50 mmol) sodium in 50 ml. ethanol. The reaction mixture is stirred for 10 minutes at ambient temperature, 6.12 g. (25 mmol) 3-(3-methoxyphenoxy)-propyl bromide, dissolved in 10 ml. ethanol, are added thereto, followed by heating under reflux for 2 hours, whereafter the solvent is distilled off. The residue is taken up in water, acidified and extracted with diethyl ether. The residue obtained after drying and evaporating the extract gives, upon trituration with diethyl ether, 5.5 g. (82% of theory) of S-[3-(3-methoxyphenoxy)-propyl]-3-mercaptopropionic acid; m.p. 53°–55° C.

EXAMPLE 4

The following compounds are obtained in a manner analogous to that described in Example 3:

| | designation | Yield % | m.p. °C. (solvent) |
|---|---|---|---|
| a | S—(2-phenoxyethyl)-L-cysteine from 2-phenoxyethyl bromide and L-cysteine | 73 | 223–225 (ethanol) |
| b | S—(3-phenoxypropyl)-3-mercaptopropionic acid from 3-phenoxypropyl bromide and 3-mercaptopropionic acid | 56 | 59–61 (ligroin) |
| c | S—[3-(4-acetylphenoxy)-propyl]-3-mercaptopropionic acid from 3-(4-acetylphenoxy)-propyl bromide and 3-mercaptopropionic acid | 80 | 125–126 (water) |
| d | S—[3-(2-propylphenoxy)-propyl]-3-mercaptopropionic acid from 3-(2-propyl-phenoxy)-propyl bromide and 3-mercaptopropionic acid | 55 | b.p. 0.4 200–202 |
| e | S—[3-(4-acetyl-2-propyl-phenoxy)-propyl]-3-mercapto-propionic acid from 3-(4-acetyl-2-propylphenoxy)-propyl bromide and 3-mercapto-propionic acid | 61 | 42–45 (water) |
| f | S—[3-(3-methoxy-5-methyl-phenoxy)-propyl]-3-mercapto-propionic acid from 3-(3-methoxy-5-methylphenoxy)-propyl bromide and 3-mercapto-propionic acid | 52 | 38–40 (ligroin) |
| g | S—[3-(3,5-dimethoxyphenoxy)-propyl]-3-mercaptopropionic acid from 3-(3,5-dimethoxy-phenoxy)-propyl bromide and 3-mercaptopropionic acid | 70 | 50–52 |
| h | S—[3-(4-acetyl-3-hydroxy-2-propylphenoxy)-propyl]-L-crysteine from 3-(4-acetyl-3-hydroxy-2-propylphenoxy)-propyl bromide and L-crysteine | 40 | 155–160 (water) |
| i | S—[4-(4-acetyl-3-hydroxy-2-propylphenoxy)-n-butyl]-L-crysteine from 4-(4-acetyl-3-hydroxy-2-propylphenoxy)-n-butyl bromide and L-cysteine | 50 | Na salt 110–120 amorphous (water) |
| j | S—[3-(3-hydroxyphenoxy)-propyl]-3-mercaptopropionic acid from 3-(3-hydroxy-phenoxy)-propyl bromide and 3-mercaptopropionic acid | 41 | b.p. 0.5 208–215 |
| k | S-(3-anilinopropyl)-3-mercaptopropionic acid from 3-anilinopropyl bromide and 3-mercaptopropionic acid | 49 | HCl salt 85–90 amorphous (ethyl acetate) |
| l | S—[3-(phenylmercapto)-propyl]-3-mercaptopropionic acid from 3-(phenyl-mercapto)-propyl bromide and 3-mercaptopropionic acid | 70 | 48–49 (ligroin) |
| m | S—[3-(4-acetyl-3-hydroxy-2-propylphenoxy)-propyl]-2-mercaptoethanol from 3-(4-acetyl-3-hydroxy-2-propyl-phenoxy)-propyl bromide and mercaptoethanol | 94 | 72–73 (diethyl ether) |

EXAMPLE 5

S-[4-(4-acetyl-3-hydroxy-2-propylphenoxy)-2-butynyl]-2-mercaptoethanol 1.41 g. (5 mmol) 4-(4-acetyl-3-hydroxy-2-propylphenoxy)-2-butynyl chloride, together with 0.38 g. (4.9 mmol) 2-mercaptoethanol, 3 g. (30 mmol) triethylamine and 5 ml. methanol are boiled under reflux for 5 hours. The reaction mixture is allowed to cool, mixed with water, acidified and extracted with dichloromethane. The combined extracts are washed neutral, dried and evaporated. For purification of the crude product, it is chromatographed on silica gel (elution agent: dichloromethane/methanol 98:2 v/v). By trituration with diethyl ether, there is obtained 1.1 g. (68% of theory) of crystalline S-[4-(4-acetyl-3-hydroxy-2-propylphenoxy)-2-butynyl]-2-mercaptoethanol; m.p. 52°–53° C.

EXAMPLE 6

The following compounds are obtained in a manner analogous to that described in Example 5:

| | designation | yield % | m.p. °C. (solvent) |
|---|---|---|---|
| a | S—[4-(4-acetyl-3-hydroxy-2-propylphenoxy)-2-butenyl]-2-mercaptoethanol from 4-(4-acetyl-3-hydroxy-2-propylphenoxy)-2-butenyl chloride and 2-mercaptoethanol | 63 | oil |
| b | S—[4-(4-acetyl-3-hydroxy-2-propylphenoxy)-2-butenyl]-mercaptoacetic acid from 4-(4-acetyl-3-hydroxy-2-propylphenoxy)-2-butenyl chloride and mercaptoacetic acid | 52 | 66–68 (ligroin) |
| c | S—[4-(4-acetyl-3-hydroxy-2-propylphenoxy)-2-butenyl]-3-mercaptopropionic acid from 4-(4-acetyl-3-hydroxy-2-propylphenoxy)-2-butenyl chloride and 3-mercaptopropionic acid | 55 | 89–91 (diethyl ether) |
| d | S—[4-(4-acetyl-3-hydroxy-2-propylphenoxy)-2-butynyl]-mercaptoacetic acid from 4-(4-acetyl-3-hydroxy-2-propylphenoxy)-2-butynyl chloride and mercaptoacetic acid | 79 | 111–112 (ligroin) |
| e | S—[4-(4-acetyl-3-hydroxy-2-propylphenoxy)-2-butynyl]-3-mercaptopropionic acid from 4-(4-acetyl-3-hydroxy-2-propyphenoxy)-2-butynyl chloride and 3-mercaptopropionic acid | 69 | 88–90 (diethyl ether) |

EXAMPLE 7

S-[3-(4-Acetyl-2-allyl-3-hydroxyphenoxy)-2-hydroxypropyl]-2-mercaptoethanol 2.58 g. (33 mmol) 2-mercaptoethanol are added to a solution of 7.45 g. (30 mmol) 3-(4-acetyl-2-allyl-3-hydroxyphenoxy)-1,2-epoxypropane in 35 ml. methanol and 12.1 g. (120 mmol) triethylamine and the reaction mixture is stirred for 3 hours at ambient temperature. The solvent is then distilled off, the residue is taken up in dichloromethane, evaporated, washed neutral and chromatographed on silica gel (elution agent: dichloromethane/methanol 9:1 v/v). After trituration with diethyl ether, there are obtained 4.5 g. (46% of theory) S-[3-(4-acetyl-2-allyl-3-hydroxyphenoxy)-2-hydroxypropyl]-2-mercaptoethanol; m.p. 54°–56° C.

EXAMPLE 8

The following compounds are obtained in a manner analogous to that described in Example 7:

| | designation | yield % | m.p. °C. (solvent) |
|---|---|---|---|
| a | S—[3-(4-acetyl-2-allyl-3-hydroxyphenoxy)-2-hydroxypropyl]-2-hydroxy-3-mercaptopropanol from 3-(4-acetyl-2-allyl-3-hydroxyphenoxy)-1,2-epoxypropane and 2-hydroxy-3-mercaptopropanol | 40 | oil |
| b | S—[3-(4-acetyl-3-hydroxy-2-propylphenoxy)-2-hydroxypropyl]-2-mercaptoethanol from S—[3-(4-acetyl-3-hydroxy-2-propylphenoxy)-1,2-epoxypropane and 2-mercaptoethanol | 64 | 56–57 (diethyl ether) |

EXAMPLE 9

S-[3-(4-Acetyl-2-allyl-3-hydroxyphenoxy)-2-hydroxypropyl]-3-mercaptopropionic acid 3.5 g. (33 mmol) 3-Mercaptopropionic acid are added to a solution of 7.45 g. (30 mmol) 3-(4-acetyl-2-allyl-3-hydroxyphenoxy)-1,2-epoxypropane in 35 ml. methanol and 12.1 g. (120 mmol) triethylamine and the reaction mixture is stirred for 10 hours at ambient temperature. Thereafter, it is evaporated, the residue is taken up in water, acidified and extracted with dichloromethane. After drying and evaporating the solution, there are obtained 7.2 g. (68% of theory) S-[3-(4-acetyl-2-allyl-3-hydroxyphenoxy)-2-hydroxypropyl]-3-mercaptopropionic acid as an oil.

When an ethanolic solution of the product obtained is mixed with an aqueous solution of L-lysine (mole ratio 1:1), the title compound is precipitated out quantitatively as the lysine salt; m.p. 96°–99° C.

EXAMPLE 10

The following compounds are obtained in a manner analogous to that described in Example 10:

| | designation | yield % | m.p. °C. (solvent) |
|---|---|---|---|
| a | S—[3-(4-acetyl-3-hydroxy-2-propylphenoxy)-2-hydroxypropyl]-L-cysteine from 3-(4-acetyl-3-hydroxy-2-propylphenoxy)-1,2-epoxypropane and L-cysteine | 51 | 141–142 (dichloromethane) |
| b | S—[3-(4-acetyl-2-allyl-3-hydroxyphenoxy)-2-hydroxypropyl]-L-cysteine from 3-(4-acetyl-2-allyl-3-hydroxyphenoxy)-1,2-epoxypropane and L-cysteine | 60 | 159–161 (decomp.) (dichloromethane) |
| c | S—[3-(4-acetyl-2-allyl-3-hydroxyphenoxy)-2-hydroxypropyl]-N-trifluoroacetyl-L-cysteine from 3-(4-acetyl-2-allyl-3-hydroxyphenoxy)-1,2-epoxypropane and N-trifluoroacetyl-L-cysteine | 56 | 75 amorphous |
| d | S—[3-(3-chlorophenoxy)-2-hydroxypropyl]-3-mercaptopropionic acid from 3-(3-chlorophenoxy)-1,2-epoxypropane and 3-mercaptopropionic acid | 31 | 58–60 (dichloromethane) |
| e | S—[3-(3-chlorophenoxy)-2-hydroxypropyl]-cysteine from 3-(3-chlorophenoxy)-1,2-epoxypropane and L-cysteine | 68 | 176–180 (diethyl ether) |
| f | S—[2-hydroxy-3-(2-propylphenoxy)-propyl]-3-mercaptopropionic acid from 3-(2-propylphenoxy)-1,2-epoxypropane and 3-mercaptopropionic acid | 78 | Na salt 60–70 amorphous (water) |
| g | S—[2-hydroxy-3-(2-propylphenoxy)-propyl]-cysteine from 3-(2-propylphenoxy)-1,2-epoxypropane and L-cysteine | 76 | 178–181 (acetone) |
| h | S-[2-hydroxy-3-(3-methoxyphenoxy)-propyl]-3-mercaptopropionic acid from 3-(3- | 75 | Na salt 40–50 amorphous |

-continued

| designation | yield % | m.p. °C. (solvent) |
|---|---|---|
| methoxyphenoxy)-1,2-epoxy-propane and 3-mercapto-propionic acid | | (water) |
| i S—[2-hydroxy-3-(3-methoxy-phenoxy)-propyl]-cysteine from 3-93-methoxyphenoxy)-1,2-epoxypropane and L-cysteine | 62 | 182 (water) |
| j S—[2-hydroxy-3-(2-pentyl-phenoxy)-propyl]-3-mercapto-propionic acid from 3-(2-pentylphenoxy)-1,2-epoxy-propane and 3-mercapto-propionic acid | 64 | Na salt 92–96 amorphous |
| k S—[2-hydroxy-3-(2-pentyl-phenoxy)-propyl]-cysteine from 3-(2-pentylphenoxy)-1,2-epoxypropane and L-cysteine | 71 | HCl salt 150–152 (water) |
| l S—[3-(4-acetyl-3-hydroxy-2-propylphenoxy-2-hydroxy-propyl]-3-mercaptopropionic acid from 3-(4-acetyl-3-hydroxy-2-propylphenoxy)-1,2-epoxypropane and 3-mercaptopropionic acid | 73 | 104–107 (dichloro-methane) |

EXAMPLE 11

N-[2-(4-Morpholino)-ethyl]-S-(2-phenoxyethyl)-mercaptoacetamide 5.2 g. (25 mmol) Phosphorus pentachloride are introduced at 10° to 15° C., within the course of 20 minutes, into a solution of 5.3 g. (25 mmol) mercapto-S-(2-phenoxyethyl)-acetic acid in dichloromethane and the mixture subsequently stirred for half an hour at ambient temperature. It is thereafter evaporated at 40° C., the residue is taken up in dichloromethane and this solution is added dropwise to a solution of 3.9 g. (30 mmol) 2-aminoethyl-morpholine and 4.2 g. (50 mmol) sodium hydrogen carbonate in 50 ml. dichloromethane. After heating under reflux for 4 hours, 50 ml. water are added thereto and stirring continued for half an hour. The organic phase is separated off, dried and evaporated. The residue is taken up in acetone and the desired compound is precipitated as the oxalate. There are obtained 8.8 g. (85% of theory) N-[2-(4-morpholino)-ethyl]-S-(2-phenoxyethyl)-mercaptoacetamide oxalate; m.p. 120°–122° C.

EXAMPLE 12

3-(4-Acetyl-3-hydroxy-2-propylphenoxy)-propyl mercaptan

A solution of 5 g. (16 mmol) 3-(4-acetyl-3-hydroxy-2-propylphenoxy)-propyl bromide and 1.33 g. (17 mmol) thiourea in 20 ml. ethanol is heated under reflux for 6 hours. The reaction mixture is allowed to cool, mixed under an atmosphere of nitrogen with 9.8 ml. (50 mmol) 5N aqueous sodium hydroxide solution and boiled under reflux for 2 hours. After acidification of the cooled reaction mixture, suction filtration and drying, there are isolated 4 g. (94% of theory) 3-(4-acetyl-3-hydroxy-2-propylphenoxy)-propyl mercaptan in the form of an amorphous product which becomes dark coloured at temperatures above 250° C.

EXAMPLE 13

S-[3-(4-Acetyl-3-hydroxy-2-propylphenoxy)-propyl]-3-mercaptopropionic acid 1.34 g. (5 mmol) 3-(4-Acetyl-3-hydroxy-2-propylphenoxy)-propyl mercaptan, 0.9 g. (6 mmol) 3-bromopropionic acid and 2.8 ml. (20 mmol) triethylamine are heated under reflux for 4 hours in 5 ml. methanol. After cooling, the reaction mixture is mixed with water, acidified and extracted with dichloromethane. The organic phase is washed neutral, dried and evaporated. The oil obtained is chromatographed on silica gel (elution agent: dichloromethane with an increasing proportion of methanol up to a maximum mixture ratio of 95:5 v/v). After trituration with diethyl ether, there is obtained 0.9 g. (47% of theory) S-[3-(4-acetyl-3-hydroxy-2-propylphenoxy)-propyl]-3-mercaptopropionic acid; m.p. 90°–92° C.

EXAMPLE 14

The following compounds are obtained in a manner analogous to that described in Example 13:

| designation | yeild % | m.p. °C. (solvent) |
|---|---|---|
| a S—[3-(4-acetyl-3-hydroxy-2-propylphenoxy)-propyl]-6-mercaptocaproic acid from 3-(4-acetyl-3-hydroxy-2-propyl-phenoxy)-propyl mercaptan (Example 12) and 6-bromo-caproic acid | 50 | Na salt 82–84 amorphous (water) |
| b S—[3-(4-acetyl-3-hydroxy-2-propylphenoxy)-propyl]-12-mercaptododecanoic acid from 3-(4-acetyl-3-hydroxy-2-propylphenoxy)-propyl mercaptan (Example 12) and 12-bromododecanoic acid | 44 | 63–65 (ligroin) |

EXAMPLE 15

S-[3-(3-Methoxy-5-methylphenoxy)-propyl]-3-mercaptopropionic acid

A solution of 3.0 g. (22 mmol) 3-methoxy-5-methyl phenol in 10 ml. dimethylformamide is added dropwise to a suspension of 2.2 g. (44 mmol) 50% sodium hydride in 50 ml. dimethylformamide, the reaction mixture is stirred for 10 minutes at ambient temperature, a solution of 3.15 g. (22 mmol) S-(3-chloropropyl)-3-mercaptopropionic acid in 10 ml. dimethylformamide is added dropwise thereto and the reaction mixture heated to 100° C. for 4 hours. It is thereafter evaporated in a vacuum, the residue is mixed with diethyl ether, extracted with water and the aqueous phase acidified and extracted with diethyl ether. After evaporation, there are obtained 2.9 g. (46% of theory) S-[3-(3-methoxy-5-methylphenoxy)-propyl]-3-mercaptopropionic acid; m.p. 39°–42° C. (recrystallised from ligroin).

EXAMPLE 16

The following compound is obtained in a manner analogous to that described in Example 15:

| designation | Yield % | m.p. °C. (solvent) |
|---|---|---|
| S—[3-(3-hydroxy-2-propyl-phenoxy)-propyl]-3-mercapto- | 30 | Na salt 40–50 |

-continued

| designation | Yield % | m.p. °C. (solvent) |
|---|---|---|
| propionic acid from 2-propyl-resorcinol and S-(3-chloro-propyl)-3-mercaptopropionic acid | | amorphous (water) |

EXAMPLE 17

3-[3-(4-Acetyl-2-allyl-3-hydroxyphenoxy)-propyl]-sulphinylpropionic acid 1.7 g. (5 mmol) S-[3-(4-Acetyl-2-allyl-3-hydroxyphenoxy)-propyl]-3-mercaptopropionic acid is mixed with a solution of 0.55 ml. (5 mmol) hydrogen peroxide in 20 ml. glacial acetic acid and the mixture stirred at ambient temperature until no more starting material can be detected by thin layer chromatography. The solvent is then distilled off in a vacuum and the residue is recrystallised from acetone. There is obtained 1 g. (56% of theory) 3-[3-(4-acetyl-2-allyl-3-hydroxyphenoxy)-propyl]-sulphinylpropionic acid; m.p. 126°–128° C.

EXAMPLE 18

The following compounds are obtained in a manner analogous to that described in Example 17:

| | designation | yield % | m.p. °C. (solvent) |
|---|---|---|---|
| a | 3—[3-(4-acetyl-3-hydroxy-2-propylphenoxy)-propyl]-sulphinylpropionic acid from S—[3-(4-acetyl-2-allyl-3-hydroxyphenoxy)-propyl]-3-mercaptopropionic acid and hydrogen peroxide | 87 | 118–121 (acetone) |
| b | 2—[3-(4-acetyl-2-allyl-3-hydroxyphenoxy)-2-hydroxypropyl]-sulphinylethanol from S—[3-(4-acetyl-2-allyl-3-hydroxyphenoxy)-2-hydroxypropyl]-2-mercaptoethanol (Example 7) and hydrogen peroxide | 83 | 142–144 (dichloromethane) |
| c | 2-[3-(4-acetyl-2-allyl-3-hydroxyphenoxy)-propyl]-sulphinylethanol from S—[3-(4-acetyl-2-allyl-3-hydroxyphenoxy)-propyl]-2-mercaptoethanol (Example 4m) and hydrogen peroxide | 70 | 95–98 (dichloromethane |
| d | 2-[3-(4-acetyl-3-hydroxy-2-propylphenoxy)-propyl]-sulphinylethanol from S—[3-(4-acetyl-3-hydroxy-2-propylphenoxy)-propyl]-2-mercaptoethanol (Example 4m) and hydrogen peroxide | 78 | 73–74 (dichloromethane) |
| e | 3-[3-(2-propylphenoxy)-propyl]-sulphinylpropionic acid from S—[3-(2-propylphenoxy)-propyl]-3-mercaptopropionic acid (Example 4d) and hydrogen peroxide | 89 | Na salt 110–120 amorphous (water) |
| f | 3-[3-(3-methoxyphenoxy)-propyl]-sulphinylpropionic acid from S—[3-(2-methoxyphenoxy)-propyl]-3-mercaptopropionic acid (Example 3) and hydrogen peroxide | 63 | Na salt 130–140 amorphous (water) |
| g | 2-[3-(4-acetyl-3-hydroxy-2-propylphenoxy)-2-hydroxypropyl]-sulphinylethanol from S—[3-(4-acetyl-3-hydroxy-2-propylphenoxy)-2-hydroxypropyl]-2-mercaptoethanol (Example 8) and hydrogen peroxide | 64 | 55–57 (diethyl ether) |
| h | 3-[3-(4-acetyl-3-hydroxy-2-propylphenoxy)-2-hydroxypropyl]-sulphinylpropionic acid from S—[3-(4-acetyl-3-hydroxy-2-propylphenoxy)-2-hydroxypropyl]-3-mercaptopropionic acid (Example 10 l) and hydrogen peroxide | 73 | 104–107 (dichloromethane/ methanol) |
| i | 3-[3-(4-acetyl-2-allyl-3-hydroxyphenoxy)-2-hydroxypropyl]-sulphinylpropionic acid from S—[3-(4-acetyl-2-allyl-3-hydroxyphenoxy)-2-hydroxypropyl]-3-mercaptopropionic acid (Example 9) and hydrogen peroxide | 80 | 137–140 (dichloromethane) |

EXAMPLE 19

3-[3-(4-Acetyl-2-allyl-3-hydroxyphenoxy)-propyl]-sulphonylpropionic acid 1.7 g. (5 mmol) S-[3-(4-Acetyl-2-allyl-3-hydroxyphenoxy)-propyl]-3-mercaptopropionic acid is mixed with a solution of 1.63 ml. (15 mmol) hydrogen peroxide in 20 ml. glacial acetic acid and stirred at ambient temperature until no more starting material can be detected by thin layer chromatography. The precipitate obtained is filtered off with suction and washed first with ethyl acetate and then with dichloromethane. There is obtained 1.2 g. (65% of theory) 3-[3-(4-acetyl-2-allyl-3-hydroxyphenoxy)-propyl]-sulphonylpropionic acid; m.p. 164°–166° C.

EXAMPLE 20

The following compounds are obtained in a manner analogous to that described in Example 19:

| | designation | yield % | m.p. °C. (solvent) |
|---|---|---|---|
| a | 3-[3-(4-acetyl-3-hydroxy-2-propylphenoxy)-propyl]-sulphonylpropionic acid from S—[3-(4-acetyl-3-hydroxy-2-propylphenoxy)-propyl]-3-mercaptopropionic acid and hydrogen peroxide | 56 | 160–162 (diethyl ether) |
| b | 2-[3-(4-acetyl-2-allyl-3-hydroxyphenoxy)-2-hydroxypropyl]-sulphonylethanol from S—[3-(4-acetyl-2-allyl-3-hydroxyphenoxy)-2-allyl-3-hydroxyphenoxy)-2-hydroxypropyl]-2-mercaptoethanol (Example 7) and hydrogen peroxide | 69 | 126–128 |

EXAMPLE 21

S-[3-(4-Acetyl-3-hydroxy-2-propylphenoxy)-2-hydroxypropyl]-2-mercapto-N,N-dimethylethylamine 7.45 g. (30 mmol) 3-(4-Acetyl-2-allyl-3-hydroxyphenoxy)-1,2-epoxypropane, dissolved in 30 ml. methanol, 6.3 g. (45 mmol) 2-dimethylaminoethyl mercaptan and 13.5 g. (135 mmol) triethylamine are mixed together and stirred for 4 hours at ambient temperature. The solvent is then distilled off, the residue is mixed with water and ethyl acetate, the extracts are shaken out three times with 1N aqueous sodium hydroxide solution and once with 1N hydrochloric acid, rendered alkaline with 2N aqueous sodium hydroxide solution and extracted three times with ethyl acetate. Washing, drying and evaporating the extracts gives 8.1 g. of oil which is chromatographed on silica gel (elution agent: dichloromethane/methanol/water 6.5:2.5:0.4 v/v/v). There are obtained 5.2 g. (48% of theory) S-[3-(4-acetyl-3-hydroxy-2-propylphenoxy)-2-hydroxypropyl]-2-mercapto-N,N-dimethylethylamine; m.p. 54°–55° C.

EXAMPLE 22

3-[3-(4-Acetyl-2-allyl-3-hydroxyphenoxy)-propyl]-sulphinylpropionic acid (2-dimethylaminoethyl)-amide 0.31 g. (3 mmol) N-methylmorpholine is added to a suspension of 1.06 g. (3 mmol) 3-[3-(4-acetyl-2-allyl-3-hydroxyphenoxy)-propyl]-sulphinylpropionic acid in 20 ml. dichloromethane and 10 ml. tetrahydrofuran, the reaction mixture is cooled to −10° C. and, at this temperature, 0.43 g. (3 mmol) isobutyl chloroformate, dissolved in 5 ml. dichloromethane, is added dropwise thereto. Subsequently, the reaction mixture is stirred for 15 minutes at −10° C. and then 0.26 g. (3 mmol) N,N-dimethylethylenediamine, dissolved in 5 ml. dichloromethane, is added dropwise thereto in such a manner that the temperature does not exceed −10° C. The reaction mixture is stirred for 1 hour at −10° C. and for 2 hours at 0° C. and then allowed to warm up to ambient temperature. The reaction mixture is mixed with water, acidified with 2N hydrochloric acid and the aqueous phase separated off and extracted twice with dichloromethane. The aqueous phase is then rendered alkaline with 2N aqueous sodium hydroxide solution, extracted three times with dichloromethane and the extracts washed neutral with water, dried and evaporated. The crude product is dissolved in methanol/dichloromethane and, by the addition of ethereal hydrochloric acid, 3-[3-(4-acetyl-2-allyl-3-hydroxyphenoxy)-propyl]-sulphinylpropionic acid (2-dimethylaminoethyl)-amide precipitated out as the hydrochloride. Yield 0.85 g. (67% of theory) as deliquescent crystals.

EXAMPLE 23

Tablets were prepared, each of which contained 10 mg. 3-[3-(4-acetyl-2-allyl-3-hydroxyphenoxy)-propyl]-sulphinylpropionic acid. The tablets were prepared according to the following formulation:

| | |
|---|---|
| 3-[3-(4-acetyl-2-allyl-3-hydroxyphenoxy)-propyl]-sulphonylpropionic acid | 10 g. |
| lactose | 80 g. |
| starch | 29 g. |
| magnesium stearate | 1 g. |

The above compound was finely pulverised and mixed with the lactose and starch. The mixture was granulated in conventional manner. Magnesium stearate was added to the granulate and the mixture pressed to give 1000 tablets, each having a weight of 0.12 g.

It will be understood that the specification and examples are illustrative but not limitative of the present invention and that other embodiments within the spirit and scope of the invention will suggest themselves to those skilled in the art.

What is claimed is:

1. Thioethers of the formula:

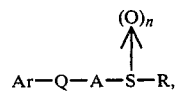
(I)

wherein Ar is 4-acetyl-3-hydroxyphenyl, 4-acetyl-2-allyl-3-hydroxyphenyl, 4-acetyl-3-hydroxy-2-propylphenyl or 2-carboxyphenyl Q is oxygen;

A is

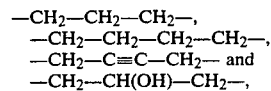

n is 0, 1 or 2, and
R is

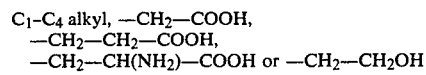

or a pharmacologically acceptable salt thereof.

2. The thioether of claim 1 wherein A is —$CH_2CH_2CH_2$— or —$CH_2$—CH(OH)—$CH_2$—.

3. The thioethers of claim 1 wherein R is —$CH_2$—COOH, —$CH_2CH_2$—COOH, —$CH_2$—CH($NH_2$)—COOH.

4. The thioethers of claim 1 wherein n is 0.

5. The thioethers of claim 1 wherein n is 0.

6. The thioether of claim 1 wherein
Ar is 4-acetyl-3-hydroxyphenyl; 4-acetyl-2-allyl-3-hydroxyphenyl; 4-acetyl-3-hydroxy-2-propylphenyl; or 2-carboxyphenyl;
Q is oxygen;
A is —$CH_2CH_2CH_2$— or $CH_2$—CH(OH)—$CH_2$;
R is —$CH_2$—COOH, —$CH_2CH_2$COOH, —$CH_2$—CN($NH_2$)—COOH or —$CH_2CH_2$OH; and
n is 0.

7. The thioether of claim 1 designated S-[3-(4-acetyl-2-allyl-3-hydroxyphenoxy)-propyl]-3-mercaptopropionic acid.

8. The thioether of claim 1 designated 2-[3-[S-(2-butyl)-mercapto]-propoxy]-benzoic acid.

9. The thioether of claim 1 designated S-[4-(4-acetyl-3-hydroxy-2-propylphenoxy)-n-butyl]-L-cysteine.

10. The thioether of claim 1, designated S-[4-(4-acetyl-3-hydroxy-2-propylphenoxy)-2-butynyl]-3-mercaptopropionic acid.

11. The thioether of claim 1 designated S-[3-(4-acetyl-2-allyl-3-hydroxyphenoxy)-2-hydroxy-propyl]-3-mercaptopropionic acid.

12. The thioether of claim 1 designated 3-[3-(4-acetyl-2-allyl-3-hydroxyphenoxy)-propyl]-sulphinylpropionic acid.

13. Pharmaceutical composition for the treatment of allergic diseases comprising an antiallergic effective amount of the thioether of claim 1 in a pharmaceutically acceptable carrier.

14. Pharmaceutical composition comprising 0.05 to 50 mg/ml of the thioether of claim 1 in an aqueous pharmaceutically acceptable injection medium.

15. Pharmaceutical composition for the treatment of allergic diseases comprising an antiallergic effective amount of a thioether compound of claim 1 selected from the group consisting of S-[3-(4-acetyl-2-allyl-3-hydroxyphenoxy)propyl]-3-mercapto-propionic acid, 2-[3-[S-(2-butyl)mercapto]-propoxy]-benzoic acid, S-[4-(4-acetyl-3-hydroxy-2-propylphenoxy)-n-butyl]-L-cysteine, S-[4-(4-acetyl-3-hydroxy-2-propylphenoxy)-2-butynyl]-3-mercaptopropionic acid, S-[3-(4-acetyl-2-allyl-3-hydroxyphenoxy)-2-hydroxypropyl]-3-mercaptopropionic acid, and 3-[3-(4-acetyl-2-allyl-3-hydroxyphenoxy)-propyl]-sulphinylpropionic acid in a pharmaceutically acceptable carrier.

* * * * *